United States Patent [19]

McDonagh et al.

[11] Patent Number: 5,637,299
[45] Date of Patent: Jun. 10, 1997

[54] ENHANCEMENT OF THROMBOLYTIC THERAPY WITH DEGLYCOSYLATED FORMS OF PLASMINOGEN

[75] Inventors: Jan McDonagh, Chestnut Hill; Myoung H. Lee, Brookline, both of Mass.

[73] Assignee: Beth Israel Hospital, Boston, Mass.

[21] Appl. No.: 461,172

[22] Filed: Jun. 5, 1995

Related U.S. Application Data

[63] Continuation of Ser. No. 227,191, Apr. 13, 1994, abandoned, which is a continuation of Ser. No. 907,260, Jul. 1, 1992, abandoned.

[51] Int. Cl.⁶ .......................... A61K 38/48; A61K 38/49; C12N 9/64; C12N 9/68
[52] U.S. Cl. .......................... 424/94.63; 424/94.64; 435/212; 435/215; 435/216; 435/217; 435/226
[58] Field of Search .................. 424/94.63, 94.64; 435/212, 215, 216, 217, 226

[56] References Cited

U.S. PATENT DOCUMENTS 4,996,050  2/1991  Tsukada et al. ...................... 424/94.2

FOREIGN PATENT DOCUMENTS 0307847  9/1988  European Pat. Off. ..
91/08297  6/1991  WIPO .

OTHER PUBLICATIONS

Lijnen et al., "On the Role of the Carbohydrate Side Chains of Human Plasminogen in Its interaction with $\alpha_2$-Antiplasmin and Fibrin", *Eur. J. Biochem.* 120:149–154 (1981).

Takada et al., "Glu–Plasminogen I and II: Their Activation by Urokinase and Streptokinase in the Presence of Fibrin and Fibrinogen:," *Thrombosis Research* 39:289–296 (1985).

Pannell et al., "Complementary Modes of Action of Tissue–Type Plasminogen Activator and Pro–urokinase by which Their Synergistic Effect on Clot Lysis May be Explained", *J. Clin. Invest.*, 81:853–859 (1988).

Watahiki et al., "Potentiation by Lys–Plasminogen of Clot Lysis by Single or Two Chain Urokinase–Type Plasminogen Activator or Tissue–Type Plasminogen Activator", *Thrombosis and Haemostasis* 61(3):502–506 (1989).

Stack et al., "Effect of desialylation on the biological properties of human plasminogen", *Biochem J.* 284:81–86 (1992).

Davidson, Donald J. et al., "Plasminogen Activator Activities of Equimolar Complexes of Streptokinase with Variant Recombinant Plasminogens," *Biochemistry*, 29:3585–3590 (1990).

Kumarasamy, R. *J. Chromatography* 512:149–155 (1990).

deVries, C. et al., *J. Biol. Chem.* 265(23):13547–13552 (1990).

Badylak, S.F. et al., *Thrombosis Research* 62:115–126 (1991).

*Primary Examiner*—Dian C. Jacobson
*Attorney, Agent, or Firm*—Hamilton, Brook, Smith & Reynolds, P.C.

[57] ABSTRACT

This invention provides an improved method for enhancing the activity of thrombolytic agents, including t-PA, scu-PA, tcu-PA, streptokinase, acylated plasminogen-streptokinase activator complex (APSAC), mixtures of these, and other activators of plasminogen. The enhancement method comprises supplementation of plasma plasminogen levels with deglycosylated forms of glu- and lys-plasminogen. Deglycosylated plasminogen refers herein to glu- or lys-plasminogen 2 having a single oligosaccharide chain at $Thr_{345}$, plasminogens having a single oligosaccharide chain at $Asn_{288}$, and unglycosylated forms of plasminogen. The work described herein shows that a less glycosylated form of plasminogen (glu-plasminogen 2) has a higher affinity for fibrin clots than a more glycosylated plasminogen (glu-plasminogen 1). Based on this work, it is believed that glycosylation of plasminogen inhibits binding of plasminogen to fibrin clots, perhaps due to steric hindrance, and further, that deglycosylated forms of plasminogen may be more effective enhancers of scu-PA in thrombolytic therapy than fully glycosylated forms of plasminogen. Improved enhancement of the activity of thrombolytic agents allows the use of lower therapeutic doses and thus, is expected to relieve some of the bleeding and other side effects of thrombolytic therapy.

16 Claims, No Drawings

ENHANCEMENT OF THROMBOLYTIC THERAPY WITH DEGLYCOSYLATED FORMS OF PLASMINOGEN

GOVERNMENT FUNDING

This work was supported by Grant No. HL33014 from the National Institutes of Health. The government has certain rights in the invention.

This application is a continuation of application Ser. No. 08/227,191, filed Apr. 13, 1994, now abandoned, which is a File Wrapper Continuation of 07/907,260 filed Jul. 1, 1992, now abandoned.

BACKGROUND

The formation and dissolution of blood clots (thrombi) are the basic processes involved in the physiological response to blood vessel injury. Blood vessel injury triggers a complex and highly regulated series of events that culminates in the cleavage of fibrinogen to fibrin monomers which spontaneously polymerize to form the matrix of the blood clot (Colman et al., "Overview of Hemostasis", in: *Hemostasis and Thrombosis; Basic Principles and Clinical Practice*, 2nd edition, J. B. Lipptncott Co., Philadelphia, 1987, pp. 3–17). Fibrinogen is cleaved by thrombin, the activated form of the zymogen prothrombin. Fibrinogen is a six chain molecule consisting of two A$\alpha$ chains, two B$\beta$ chains and two $\gamma$ chains; cleavage by thrombin results in the release of fibrinopeptides A and B (FPA and FPB) from the amino-termini of the A$\alpha$ and B$\beta$ chains. Thrombin also activates Factor XIII$_a$ which cross-links the fibrin clot and increases its resistance to fibrinolysis. Circulating thrombin is inactivated by antithrombin III, thus, preventing systemic coagulation of the blood.

A small amount of plasma plasminogen binds to or is incorporated in the fibrin clot. Plasminogen is also a zymogen and its activated form, plasmin, is the main agent of fibrinolysis. Plasminogen is activated by plasminogen activators which are secreted from endothelial cells or other organs. Circulating plasmin does not prevent clot formation due to inhibition by $\alpha_2$-antiplasmin; however, plasmin formed on the surface of the clot appears to be protected from inhibition and degrades fibrin. The inhibitory activities of antithrombin III and $\alpha_2$-antiplasmin localize the coagulative and fibrinolytic processes to the wound site. Dissolution of the clot is part of the recovery phase and prepares for endothelial cell regrowth and vessel recanalization.

The processes of clot formation and dissolution are carried out and regulated by a complex hemostatic system which includes platelets, endothelial cells, adhesive proteins, and numerous zymogen-activators and protein inhibitors. The concerted action of this system determines a delicate balance between the antagonistic processes of clot formation and dissolution. Thus, it is not surprising that many pathological disorders arise from dysfunction in this system.

The pathological condition characterized by dysfunctional formation of blood clots is referred to as thrombosis. Thrombosis is a pathogenic component of many cardiovascular disorders, including ischaemic heart disease (myocardial infarction and sudden coronary death), stroke, and peripheral vascular disorders, such as deep-vein thrombosis and thrombophlebitis (Marder and Sherry, *N.E.J. of Med.* 318(24):1585–1595 (1988); Cook and Ubben, *Trends in Pharmacological Science* 11:444–451 (1990)). Elevated plasma fibrinogen has been found to have a stronger association with ischaemic heart disease than blood cholesterol levels (Meade et al., *The Lancet* ii:533–537 (1986)) and also appears to be a significant diagnostic factor for the severity of atherosclerosis. In addition, high fibrinogen appears to be related to cancer, inflammatory disease, and the patency of transplant grafts. The pathological mechanism of thrombosis is not well understood.

Clinical treatment of thrombosis has consisted mainly of administering thrombolytic agents intravenously or locally by catheter (see Marder and Sherry, *N.E.J. of Med.* 318(24):1512–1520 and 318(24):1585–1595 (1988) for review). The thrombolytic agents currently used: streptokinase, acylated plasminogen-streptokinase activator complex (APSAC), tissue type plasminogen activator (t-PA), and urokinase plasminogen activator (u-PA), are all plasminogen activators. Urokinase plasminogen activator, a two chain protein, is usually administered as the recombinant pro-urokinase or single chain form (scu-PA), which forms a two chain urokinase (tcu-PA) on the clot. t-PA and scu-PA have been shown, in vitro and in animal models, to be fibrin-specific, i.e., they selectively activate fibrin-bound plasminogen while leaving systemic plasminogen mainly unaffected. Thrombolytic therapy with t-PA or scu-PA, however, suffers significant shortcomings. The therapeutic dose of these plasminogen activators has been found to be high, leading to a loss of fibrin-specificity and some systemic fibrinolytic activity, as evidenced by a drop in plasma fibrinogen levels upon dosage. As a result, thrombolytic therapy with t-PA and scu-PA is often complicated by hemorrhaging.

Some attempts have been made to improve thrombolytic therapy by increasing the fibrin-specificity and/or thrombolytic activity of t-PA and scu-PA. One suggested improvement is combining t-PA and scu-PA. This is based on the possible synergism between the thrombolytic activities of t-PA and scu-PA. This synergism has been explained by the different mechanisms of action of the two plasminogen activators (Pannell et al., *J. Clin. Invest,* 81:853–859 (1988)). t-PA binds strongly to fibrin, thus, forming a complex with the plasminogen also bound to the fibrin clot. scu-PA, on the other hand, does not bind significantly to fibrin clots in plasma. Its selectivity for fibrin-bound plasminogen apparently results from a conformational change in plasminogen upon binding to fibrin which renders it more sensitive to activation by scu-PA. t-PA and scu-PA seem to activate different species of plasminogens bound to the fibrin clot. t-PA acts on plasminogens bound to internal lysine residues of fibrin, while scu-PA acts on plasminogens bound to terminal lysine residues. Thus, the t-PA and scu-PA activities complement each other and together, have increased thrombolytic activity without decreased fibrin-specificity.

Another suggested improvement is enhancement of scu-PA therapy with plasminogen (U.S. Pat. No. 4,996,050, by Tsukada et al., Feb. 26, 1991). Plasminogen has been found to increase the fibrinolytic activity of scu-PA without causing increased systemic fibrinolysis (i.e., a drastic drop in plasma fibrinogen levels). Enhancement of scu-PA activity permits lowering the dose of scu-PA and may result in less side effects.

A further suggested development of plasminogen enhancement is supplementation with lys-plasminogen in place of glu-plasminogen (EP 307,847, by Kakkar et al., Mar. 22, 1989; Watahiki et al., *Thrombosis and Haemostasis* 61:502–506 (1989)). Lys-plasminogen is an 8 kDa degraded form of glu-plasminogen (92 kDa), with the NH$_2$-terminus at Lys$_{77}$. It does not normally occur in plasma and is generated in small amounts during thrombolytic therapy. Lys-plasminogen has been found to be more sensitive to activation by tcu-PA and scu-PA and to have a higher affinity for fibrin clots than native glu-plasminogen. Supplementation with lys-plasminogen was found to result in greater enhancement of scu-PA activity than supplementation with glu-plasminogen. Glu-plasminogen was slightly more effective than lys-plasminogen at enhancing fibrinolysis by scu-PA/t-PA mixtures. Addition of low concentrations of tcu-PA has also been shown to have a synergistic effect on scu-PA activity. Glu- and lys-plasminogen were found to have equivalent enhancement of scu-PA/tcu-PA mixtures. Enhancement by lys-plasminogen was not accompanied by a significantly greater decrease in fibrinogen than observed with glu-plasminogen.

SUMMARY OF THE INVENTION

This invention provides an improved method for enhancing the activity of thrombolytic agents, including t-PA (single or two chain), scu-PA, tcu-PA, streptokinase, acylated plasminogen-streptokinase activator complex (APSAC), mixtures of these, and other activators of plasminogen. Preferably, the plasminogen activator is produced by recombinant DNA techniques. The enhancement method comprises supplementation of plasma plasminogen levels with deglycosylated forms of glu- and lys-plasminogen. Deglycosylated plasminogen refers herein to glu- or lys-plasminogen which is less glycosylated than the fully glycosylated plasminogen type 1, and includes glu- or lys-plasminogen 2 having a single oligosaccharide chain at $Thr_{345}$, plasminogens having a single oligosaccharide chain at $Asn_{288}$, and unglycosylated forms of plasminogen.

The work described herein shows that a less glycosylated form of plasminogen (glu-plasminogen 2) has higher affinity for fibrin clots than a more glycosylated plasminogen (glu-plasminogen 1). This was shown in binding of plasminogen to both normal fibrin clots and to thrombolytically resistant clots made with mutant fibrinogen Boston (Boston clots) or with normal fibrinogen under conditions of high fibrinogen and low thrombin (HFLT clots). As further described herein, binding of plasminogen to the resistant clots is impaired by incompletely cleaved fibrinogen incorporated into the fibrin clot. The binding of the less glycosylated plasminogen to the resistant clots was impaired only about half that of the more glycosylated plasminogen.

Based on this work, it is believed that glycosylation of plasminogen inhibits binding of plasminogen to fibrin clots, perhaps due to steric hindrance, and further, that less glycosylated and unglycosylated forms of plasminogen may be more effective enhancers in thrombolytic therapy than fully glycosylated forms of plasminogen. Improved enhancement of the activity of thrombolytic agents allows the use of lower therapeutic doses and thus, is expected to relieve some of the bleeding and other side effects of thrombolytic therapy.

DETAILED DESCRIPTION OF THE INVENTION

This invention provides an improved method for enhancing the activity of thrombolytic agents, including t-PA (single or two chain), scu-PA, tcu-PA, streptokinase, acylated plasminogen-streptokinase activator complex (APSAC), mixtures of these, and other activators of plasminogen. Preferably, the plasminogen activator is produced by recombinant DNA techniques. The enhancement method comprises supplementation of plasma plasminogen levels with deglycosylated forms of glu- and lys-plasminogen. Deglycosylated plasminogen refers herein to glu- or lys-plasminogen which is less glycosylated than the fully glycosylated plasminogen type 1, and includes glu- or lys-plasminogen 2 having a single oligosaccharide chain at $Thr_{345}$, plasminogens having a single oligosaccharide chain at $Asn_{288}$, and unglycosylated forms of plasminogen.

The work described herein shows that a less glycosylated form of plasminogen (glu-plasminogen 2) has higher affinity for fibrin clots than a more glycosylated plasminogen (glu-plasminogen 1). This was shown in binding of plasminogen to both normal fibrin clots and to thrombolytically resistant clots made with mutant fibrinogen Boston (Boston clots) or with normal fibrinogen under conditions of high fibrinogen and low thrombin (HFLT clots). As further described herein, binding of plasminogen to the resistant clots is impaired by incompletely cleaved fibrinogen incorporated into the fibrin clot. The binding of the less glycosylated plasminogen to the resistant clots was impaired only about half that of the more glycosylated plasminogen.

Based on this work, it is believed that glycosylation of plasminogen inhibits binding of plasminogen to fibrin clots, perhaps due to steric hindrance, and further, that less glycosylated and unglycosylated forms of plasminogen may be more effective enhancers of thrombolytic therapy than fully glycosylated forms of plasminogen. Improved enhancement of the activity of thrombolytic agents allows the use of lower therapeutic doses and thus, is expected to relieve some of the bleeding and other side effects of thrombolytic therapy.

Specifically, glu- and lys-plasminogen with a single oligosaccharide chain, including glu- and lys-plasminogen 2, and unglycosylated glu- and lys-plasminogens are claimed in this invention. Glu-plasminogen 1 has a galactosamine-based oligosaccharide at $Thr_{345}$ and a complex glucosamine-based oligosaccharide at $Asn_{288}$. Glu-plasminogen 2 has only the oligosaccharide chain at $Thr_{345}$ (Hayes and Castellino, *J. Biol. Chem.* 254(18):8772–8776, 8777–8780 (1979)).

Glu- and lys-plasminogen (types 1 and 2) can be isolated from plasma as described below in Materials and Methods. However, it is preferable to use recombinant plasminogens in patients to avoid viral and other contamination. Recombinant plasminogens can be produced by expressing the coding sequences of glu- or lys-plasminogen in any of a variety of expression vector/host cell systems which are published or commercially available. The coding sequence of glu- and lys-plasminogen are described in Sottrup-Jensen et al., *Prog. Chem. Fibrinolys, Thrombolys.* 3:191 (1977) and Malinowski et al., *Biochemistry* 23:4243 (1984), which are incorporated by reference. Nucleic acid encoding glu- and lys-plasminogen can be obtained by a number of recombinant DNA techniques, including polymerase chain reaction and chemical synthesis. Glycosylated plasminogen can be produced only in host cells which produce carbohydrates, such as Chinese Hamster Ovary (CHO) cells.

Plasminogen can be deglycosylated by various means, for example, by in Vitro treatment with neuraminadase followed by treatment with O-Glycanase, N-Glycanase, or both Glycanases (all from Genzyme Corporation, Boston, Mass.). O-Glycanase hydrolyzes Thr-linked oligosaccharides and N-Glycanase hydrolyzes Asn-linked oligosaccharides. Fully glycosylated plasminogen (plasminogen 1) can be treated with one of the two Glycanases to obtain plasminogens with a single oligosaccharide chain at either $Asn_{288}$ or $Thr_{346}$ (plasminogen 2). Treatment with both Glycanases will yield unglycosylated plasminogen.

Alternatively, unglycosylated plasminogen can be obtained by expressing the nucleic acid encoding glu- or lys-plasminogen in *E. coli* or other host cells which do not glycosylate proteins, or by genetically altering the coding sequence of plasminogen so as to lose the glycosylation sites at $Asn_{288}$ and $Thr_{345}$ and expressing the mutant recombinant plasminogen in a variety of host organisms.

Plasminogens with varying degrees of glycosylation or mixtures of these plasminogens are expected to differentially enhance thrombolysis. Thus, this invention provides a way to modulate thrombolytic agents in therapy.

Mutant glu- and lys-plasminogens with varying degrees of affinity for fibrin clots can also be produced by known mutagenesis and recombinant DNA techniques (see, e.g., Ausubel et al., eds., *Current Protocols in Molecular Biology*, Greene Publishing Associates and Wiley-Interscience, New York). The mutant plasminogens may also be used as modulatable enhancers of thrombolytic therapy.

The type 2 and other deglycosylated plasminogens can be administered as described previously (e.g., U.S. Pat. No. 4,996,050, by Tsukada et al., Feb. 26, 1991; EP 307847, by Kakkar et al., Mar. 22, 1989; these patents are incorporated by reference.) Adjustments of therapeutic dosages of the plasminogens and thrombolytic agents may be necessary for obtaining the optimal thrombolysis with minimal systemic fibrinolysis.

Described below in further detail are in vitro studies on thrombolytically resistant Boston and HFLT clots, the model for impaired plasminogen binding leading to impaired thrombolysis, and the differential binding of glu-plasminogens 1 and 2 to normal and resistant clots. The following materials, methods, and studies support and illustrate the invention; they are not intended to be limiting in any way.

MATERIALS AND METHODS

Materials

Trisma base, trifluoracetic acid (TFA), EACA (6-amino-hexanoic acid), and aprotinin were from Sigma (St. Louis, Mo.); $(NH_4)_2SO_4$ was from ICN (Cleveland, Ohio): acetonitrile was from Fisher (Fair Lawn, N.J.); Gelatin-Sepharose, Lysine-Sepharose were from Pharmacia (Piscataway, N.J.). Human thrombin (specific activity=4,250 National Institutes of Health (NIH) U/mg) was purchased from Enzyme Research Laboratory (South Bend, Ind.). Reptilase, *Agkistrodon contortrix* thrombin-like enzyme (ACTE), urokinase, two-chain tissue plasminogen activator (t-PA), and Spectrozyme-tPA were purchased from American Diagnostica (Greenwich, Conn.). Chromogenic substrate, S-2390 was from Kabi (Franklin, Ohio). All other reagents were of the highest purity commercially available.

Fibrinogen Purification

Normal fibrinogen was purified from fresh frozen plasma (American Red Cross, Northeast Division, Dedham, Mass.) anticoagulated with acid-citrate-dextrose by repeated precipitation with $(NH_4)_2SO_4$ according to a method modified from Gralnick et al. (Gralinick et al., *Thromb. Diath. Haemorrh.* 29:562 (1973)). Aprotinin was added to the plasma (10 KIU/ml of plasma) and was made deficient in fibronectin and plasminogen by passage over a gelatin-Sepharose and a lysine-Sepharose column, respectively. The effluent was precipitated with 25% saturation of $(NH_4)_2SO_4$ and the pellet was washed with 1 M $(NH_4)_2SO_4$. Precipitation and wash steps were repeated twice as described previously (Lee et al., *Blood* 78:1744 (1991)). The final pellet was dissolved in Tris-saline (0.05 M Tris-HCL, 0.1 M NaCl, pH 7.3) and dialyzed against Tris-saline. Fibrinogen concentration was determined spectrophotometrically at 280 nm with an $E^{1\%}_{1\ cm}=15.1$ and Mr=340,000 (Blomback et al., *Ark. Kemmi.* 10:415 (1956)).

Fibrinogen Boston was likewise purified from the patient's fresh plasma. Sodium dodecyl sulfate-polyacrylamide gel electrophoresis (SDS-PAGE) was performed by the method of Laemmli on 3% to 12% mini-slab gels on both reduced and nonreduced gels (Laemmli, *Nature* 227:680 (1970)). Purity and apparent molecular weight of fibrinogen Boston and its three chains were indistinguishable from the normal control fibrinogen.

A population of abnormal molecules found only in fibrinogen Boston was isolated by using reptilase (Pozdnjakava et al., *Thromb. Res.* 16:283 (1979)). Fibrinogen Boston (5 mg/ml in Tris-saline) was incubated with 0.01 U/ml reptilase at 37° C. for two hours, and the clot was removed by centrifugation. The supernatant was precipitated with 25% $(NH_4)_2SO_4$ twice to remove any residual reptilase and to concentrate the fibrinogen. The precipitate was dissolved in Tris-saline and dialyzed.

A population of desBB-abnormal fibrinogen was prepared by using the snake venom enzyme ACTE (Herzig et al., *J. Lab. Clin. Med.* 76:451 (1970)). Pure abnormal fibrinogen (4 mg/ml in Tris-saline) was incubated with 0.01 U/ml ACTE at 37° C. for eight hours, and to ensure a complete release of FPB, FPB release was monitored by HPLC every two hours. The fibrinopeptides were detected at 215 nm with a model 441 system controlled by a model 510 microprocessor (Waters system) on a µbond $C_{18}$ cartridge (0.8×10 cm, Waters) using a linear gradient of 15%–20% acetonitrile containing 0.1% trifluoroacetic acid.

Fibrinopeptide Release Analysis

Fibrinopeptide release was monitored by reverse-phase C18-HPLC and spectrophotometry at 215 nm as previously described (Lee et al., *Blood* 78:1744 (1991)).

Polymerization of Purified Fibrinogen

Polymerization was measured turbidimetrically at 350 nm with Beckman DU-65 spectrophotometer at 37° C. Fibrin clots for turbidity measurements were formed directly in 10 mm disposable polystyrene cuvettes (Bio-Rad) by mixing 1 ml of purified fibrinogen solutions with 0.01 ml of thrombin solution or reptilase (5.0 units/ml).

Isolation of Plasminogen Types 1 and 2 and Plasmin

Plasminogen was prepared from fresh frozen human plasma by affinity chromatography on lysine-Sepharose column (Deutsch and Mertz, *Science* 170:1095 (1970)) with a slight modification of the gradient elution step (Brockway and Castellino, *Arch. Biochem. Biophys.* 351:194 (1972)). Two units of fresh frozen plasma with 5,000 KIU aprotinin were loaded on a lysine-Sepharose column (2.5×24 cm), and plasminogen 1 and 2 were eluted with a 6-amino-hexanoic acid (EACA) gradient (0–10 mM) (Brockway and Castellino (1972) supra). Pooled fractions of glu- and lys-plasminogen 1 and 2 were separately precipitated with 50% $(NH_4)_2SO_4$ precipitation and dialyzed against 0.1 M potassium phosphate buffer, pH 6.0, containing 0.2 M NaCl and 20 KIU aprotonin/ml. Each of the two pools was separately applied on aminohexyl-Sepharose 4B column to separate glu- from lys-plasminogen according to the published method (Nieuwenhuizen and Traas, *Thromb. Haemostas.* 61:208 (1989)). Purity was analyzed by SDS-PAGE and $NH_2$-terminal amino acid sequence was analyzed to confirm that glu-plasminogen was not contaminated with lys-plasminogen. The plasminogen concentration was measured spectrophotometrically with $E^{1\%}_{1\ cm}=16.1$ and Mr=92,000 for glu-plasminogen (Wallen and Wiman, *Biochim. Biophys. Acta* 221:20 (1970)).

Plasmin was prepared according to the published method (Nesheim et al., *J. Biol. Chem.* 265:21,541–21,548 (1990)) by incubation of plasminogen with urokinase.

Direct Binding of t-PA or Plasminogen to Fibrin

Under the various experimental conditions, a total of 0.2 ml of fibrinogen, thrombin and either plasminogen or t-PA was incubated with 1 mg/ml albumin in Tris-Tween buffer (0.01% Tween 80 in Tris-saline) in Eppendorf tubes at 37° C. At the end of the incubation, the sample tubes were centrifuged for 5 minutes at 10,000 rpm using a table-top microcentrifuge in order to separate fibrin clots from the liquid. Aliquots were taken from the supernatants to analyze unbound fractions for either t-PA or plasminogen, as well as from the controls which contained no fibrinogen or thrombin. To inhibit non-specific plasminogen binding to the fibrin clots, 2 mM of EACA was included.

The unbound fraction of t-PA activity was determined using a chromogenic substrate, Spectrozyme-tPA. The assay mixture of 0.2 ml in Tris-Tween contained 0.5 mM of Spectrozyme-tPA and 5–10 µl of supernatant from the binding study experiments. The increase of absorbance at 405 nm at 37° C. was monitored on microplate reader (Molecular Devices, Menlo Park, Calif.). The bound fraction of t-PA was calculated by subtracting the supernatant activity from the control activity.

The unbound fraction of plasminogen was determined by converting plasminogen to plasmin by urokinase, then, measuring plasmin activity using a chromogenic substrate, S-2390. Aliquots of supernatant were incubated with 100 U/ml urokinase at 37° C. for two hours in 50 mM sodium phosphate buffer with 20% glycerol, pH 8.0. Plasmin activity of the incubation mixture was determined spectrophotometrically with 0.3 mM S-2390 as described above for t-PA activity.

Dissolution of Fibrin Clots

Normal and Fibrinogen Boston clots were formed in microplate with various concentrations of thrombin in 0.1 ml of Tris-Tween buffer at 37° C. On top of the fibrin clots, 0.1 ml of plasmin, t-PA, or plasminogen in Tris-Tween was added, and the clearance of the gel was monitored at 37° C. for decrease in the absorbance at 405 nm on microplate reader.

STUDY 1

Case Report of Patient Source of Fibrinogen Boston

Fibrinogen Boston was discovered in a 63 year old woman with recurrent thromboembolism. She was moderately obese and otherwise appeared to be healthy except for adult onset diabetes. She has been on Coumadin for ten years. At age 52, she was hospitalized for a history of phlebitis which has been treated with bedrest alone. Two years later, she was admitted again with the problem of an embolus in the mid-popliteal artery at the level of the knee and a fresh thrombus in the distal popliteal origin which extended into the origin of the trifurcation vessels. Intra-arterial streptokinase infusion for twelve hours did not change her clinical status, which led to a right femoral embolectomy; an additional embolus was found in the origin of the common femoral artery which was removed with good prograde flow. Since then, she has remained on Coumadin in a dose of 5 mgs. daily. Her clinical test results indicated that she had dysfibrinogenemia: thrombin time (46 seconds) and reptilase time (78 seconds) were prolonged with low functional (90 mg/dl) and high immunological (440 mg/ml) plasma fibrinogen levels. Negative euglobulin clot lysis at 120 minutes with a normal plasminogen of 3.8 CTA indicated that she was probably dysfibrinogenemic with defective fibrinolysis.

STUDY 2

Fibrinopeptide Analyses of Purified Fibrinogen Boston

Release of total fibrinopeptides from purified normal and Fibrinogen Boston by high concentration of thrombin (5 U/ml) was examined. Compared to normal control fibrinogen, fibrinogen Boston released about 50% of normal FPA and FPAp with additional HPLC peaks denoted as FPA' and FPAp'. FPAp is the phosphorylated form of FPA. Amino acid sequence analysis of the FPA' and FPAp' peaks identified abnormal peptides with an $Arg_{16}$ to His substitution in the Aα chain. Total FPA release by reptilase was examined. Only normal FPA was released at a level of about 50% of the total FPA in control fibrinogen. Reptilase did not cleave abnormal FPA' as previously reported (Glanakiset et al., Ann. N, Y. Acad. Sci. 408:644 (1983)).

Fibrinopeptide release by 0.5 U/ml thrombin was monitored at incubation times of up to 1 hour, at 2 hours, and overnight. The time course of fibrinopeptide release from normal and fibrinogen Boston showed that the abnormal peptides, FPA' and FAp', were released more than 100 times more slowly than the normal peptides, FPA and FPAp. FPB from the abnormal part of fibrinogen Boston was released before the FPA' and FPAp', suggesting that, in this case, FPB release is not totally dependent on, or sequential to FPA release, as proposed in the case of normal fibrinogen (Higgins et al., J. Biol. Chem. 258:9276 (1983)). After overnight incubation, all FPA' and FPAp' were completely released.

STUDY 3

Polymerization of Purified Fibrinogen Boston

Fibrinogen Boston displayed delayed polymerization with both thrombin and reptilase. With 2 U/ml thrombin, fibrinogen Boston showed somewhat delayed polymerization, but the end amount of gelation was almost the same as the control fibrinogen, indicating that under this experimental condition, all the FPA' was eventually released, leading to normal fibrin formation. In contrast, with low thrombin concentration (0.1 U/ml), polymerization of fibrinogen Boston was very slow, and the end amount of gelation was about half that of normal fibrinogen; half of the fibrinogen Boston is not releasing FPA' under this condition. When the concentration of fibrinogen Boston was doubled compared to that of normal controls, surprisingly, polymerization of fibrinogen Boston was much more inhibited and the end amount was much lower than with normal fibrinogen. It appears that the abnormal population in fibrinogen Boston inhibits fibrin polymerization. The addition of $Ca^{+2}$ ions did not reverse the inhibition of polymerization.

STUDY 4

Binding of t-PA to Boston Fibrin Clots

In preliminary experiments, clots made with a normal crude fibrinogen preparation dissolved in three hours at 37° C., while clots made with crude fibrinogen Boston remained intact overnight, indicating that fibrinogen Boston is associated with impaired fibrin-mediated plasminogen activation. This finding led to further investigation of the fibrinolytic properties of this abnormal fibrinogen.

The binding of t-PA to normal and Boston fibrin clot was studied using high and low thrombin concentrations to induce fibrin clots. Based on the fibrinopeptide release data, high thrombin leads to nearly complete proteolysis of FPA' from the abnormal fibrinogen in fibrinogen Boston and low thrombin leads to little proteolysis of the abnormal fibrinogen. Table 1 shows the data for t-PA binding to normal and fibrin Boston with 0.1 U/ml thrombin at 37° C. for 2 hours.

TABLE 1 t-PA Binding to Fibrin Clots

| | Normal Clots (mg/ml) | | | Boston Clots (mg/ml) | | |
|---|---|---|---|---|---|---|
| | 1 | 3 | 5 | 1 | 3 | 5 |
| | % Bound | | | | | |
| t-PA | 72 | 74 | 78 | 52 | 50 | 69 |

As shown in Table 1, t-PA binding to normal fibrin and fibrin Boston did not differ significantly, and was not affected by fibrinogen concentration (1–5 mg/ml). Apparently, the two different conditions, where most of the abnormal fibrinogen in fibrinogen Boston is cleaved or most uncleaved, did not change t-PA binding to these different forms of fibrins. Since t-PA binding to fibrin is very tight, (the kinetically determined binding constant is 20 nM), clots having various forms and concentrations of fibrin may bind well to t-PA.

STUDY 5

Binding of Plasminogen to Fibrin Clots

The binding of two glycosylated forms of plasminogen to fibrin clots was examined. Glu-plasminogen type 1 contains a biantennary complex oligosaccharide at $Asn_{288}$, and glu-plasminogen type 2 contains only one O-linked oligosaccharide at $Thr_{345}$ (Castellino, Bioscience 33:647–650 (1983); Hayes and Castellino, J. Biol. Chem. 254:8768–8771 (1979); Hayes and Castellino, J. Biol. Chem. 254:8772–8776 (1979); Hayes and Castellino, J. Biol. Chem. 254:8777–8780 (1979)). N-terminal amino acid sequence analysis showed that glu-plasminogens 1 and 2 were isolated without any detectable level of lys-plasminogen. Purified glu-plasminogens 1 and 2 were analyzed by SDS-PAGE.

Plasminogen binding to fibrin clots made with various concentrations of normal and fibrinogen Boston was examined (Table 2). The experimental condition was set such that most of the FPA' in fibrinogen Boston is uncleaved (i.e., low thrombin). Non-specific plasminogen binding to the fibrin clots in the presence of 2 mM EACA was only about 1–5%; therefore, non-specific binding was not subtracted for the control.

TABLE 2

Plasminogen Binding to Fibrin Clots

| | Normal Clots (mg/ml) | | | Boston Clots (mg/ml) | | |
|---|---|---|---|---|---|---|
| | 1 | 3 | 5 | 1 | 3 | 5 |
| | % Bound | | | | | |
| plg-1 | 47 | 45 | 51 | 17 | 1 | 4 |
| plg-2 | 68 | 70 | 61 | 75 | 60 | 40 |

As shown in Table 2, plasminogen 2 bound more tightly to both normal and Boston clots than plasminogen 1. It appears that there is a steric hinderance for the plasminogen 1 binding to fibrin, which is probably due to the presence of the extra biantennary oligosaccharide at $Asn_{288}$.

Binding of plasminogen 1 (about 48%) and plasminogen 2 (about 66%) to normal fibrin did not change much with increasing fibrinogen concentration (1 to 5 mg/ml). It is surprising that as fibrinogen Boston concentration was increased, the binding of glu-plasminogens 1 and 2 decreased. With 3 mg/ml fibrinogen Boston, almost no plasminogen 1 binding was detected and plasminogen 2 binding to fibrin Boston decreased about 2 × when the fibrinogen concentration was 5 mg/ml. This finding indicates that intact abnormal fibrinogen in Boston clots inhibited the binding of plasminogen to fibrin, since the clots were formed under conditions such that only the normal population of fibrinogen in fibrinogen Boston would release fibrinopeptides, while most of the abnormal population of fibrinogen was intact. It is possible that, as normal fibrin slowly forms fibrin clots, abnormal fibrinogen is excluded from the clot and incorporated on the fibrin surface; therefore, as fibrinogen Boston concentration is raised higher, abnormal fibrinogen level accumulates on the fibrin surface and inhibits plasminogen binding.

In order to verify this hypothesis, plasminogen 1 binding to fibrin Boston was studied either with increasing incubation time and fixed 0.2 U/ml thrombin, or increasing thrombin concentration (0.2 U/ml to 2 U/ml thrombin) and fixed incubation time (two hours) (Table 3).

TABLE 3

A. Plasminogen 1 Binding At Various Incubation Times

| | Incubation (Hours) | | | |
|---|---|---|---|---|
| | 1 | 2 | 4 | 8 |
| | % Bound | | | |
| Normal Clots | 38 | 46 | 47 | 48 |
| Boston Clots | 0 | 10 | 33 | 43 |

B. Plasminogen 1 Binding At Various Thrombin Concentrations

| | Thrombin (U/ml) | | |
|---|---|---|---|
| | 0.2 | 0.5 | 2 |
| | % Bound | | |
| Normal Clots | 49 | 46 | 48 |
| Boston Clots | 13 | 16 | 26 |

As shown in Table 3, plasminogen 1 binding to normal fibrin did not change with higher thrombin concentrations or prolonged incubation times, but plasminogen 1 binding to fibrin Boston increased under these conditions, as abnormal fibrinogen released more fibrinopeptides. These data indicate that abnormal fibrinogen in fibrin Boston inhibits the binding of plasminogen to fibrin clots.

In order to verify the effect of abnormal fibrinogen on plasminogen binding to normal fibrin, clots were made from a mix of normal and fibrinogen Boston (Table 4). Since some desBB-fibrinogen forms from abnormal fibrinogen, the effect of both the abnormal fibrinogen and desBB-fibrinogen on the binding of plasminogens 1 and 2 to normal fibrin was studied. Pure desBB-abnormal fibrinogen was prepared by ACTE treatment of abnormal fibrinogen which was isolated from fibrinogen Boston using reptilase. Interestingly ACTE did not cleave abnormal fibrinopeptide A' (Aα $His_{16}$), while it cleaved normal FPA from normal fibrinogen with a preference for FPB to FPA of about 3 to 1 (Herzig et al., J. Lab. Clin. Med. 76:451 (1970)).

Normal fibrinogen (2 mg/ml) was mixed with abnormal or desBB-abnormal fibrinogen (2 mg/ml) and incubated with 0.1 U/ml thrombin for two hours. Under this condition, all FPA' remains uncleaved and only normal fibrinogen releases FPA completely.

TABLE 4

Inhibition of Plasminogen Binding To Normal Fibrin By Abnormal Fibrinogen

| | Normal Fibrin | + Abnormal Fbg | + DesBB Fbg |
|---|---|---|---|
| | | % Bound | |
| Plg 1 | 35 | 0 | 0 |
| Plg 2 | 76 | 35 | 25 |

As shown in Table 4, the presence of either abnormal- or desBB-fibrinogen completely inhibited binding of plasminogen 1 on the surface of the fibrin clot and decreased plasminogen 2 binding about 2 ×.

Recently, Shainoff et al. (*Blood Coagulation and Fibrinolysis* 1:499–503 (1990)) reported that fibrinogen dimers rather than fibrin dimers are predominantly detected in the plasma of subjects with occlusive vascular disease. They predicted that levels of Aα-chain dimers in blood may be closely correlated with atherosclerotic vascular disease. The data presented herein also suggest that fibrinopeptide A attached on abnormal fibrinogen or desBB-fibrinogen inhibits plasminogen binding to the fibrin clot surface. Fibrin clot dissolution data with t-PA and plasminogen also show that fibrin Boston was degraded more slowly than normal fibrin (see below).

STUDY 6

Dissolution of Boston Fibrin Clots

Clots were formed in microplate under various experimental conditions. 0.1 ml of t-PA (0.01 mg/ml) and plasminogen (0.05 mg/ml) solution was added to the top of the clots, and the clearance of the clots was monitored by spectrophotometry at 405 nm. The initial rate of dissolution of Boston clots was about 10 × slower than that of normal fibrin and had a slightly longer lag time.

Since plasminogen binding to fibrin Boston was impaired, plasmin binding was suspected to be defective. Experimental results confirmed that dissolution of fibrin Boston by plasmin was much slower than normal fibrin. Interestingly, there was a long lag time before onset of plasmin degradation of fibrin Boston, whereas normal fibrin was degraded without any delayed lag time. When plasmin concentration was increased 5 ×, the lag time with fibrin Boston was shortened by about 5 × and the dissolution rate was very similar to that of normal fibrin. These data strongly suggest that abnormal fibrinogen on the surface of the fibrin clot inhibits the interaction of plasmin with the fibrin clot, and that once fibrinogen is degraded by plasmin, probably with the removal of fibrinopeptide A region, plasmin interaction to fibrin becomes normal.

STUDY 7

Plasminogen Binding of Another Dysfibrinogemia (Boston II)

It is known that many diabetic patients have thrombotic problems. Interestingly, diabetic patients often have extra glycosylation of plasma proteins (McDonald et al., *J. Biol. Chem.* 252:2992 (1977); McVerry et al., *Haemostasis* 10:261 (1981); Urbanowski et al., *J. Biol. Chem.* 257:111 (1982)). To exclude any possibility that diabetes in the present study is another factor for the defective plasminogen binding to fibrin, fibrinogen was purified from another patient who has the same dysfibrinogenemia (fibrinogen Boston II) with a slight bleeding disorder. The same result, i.e., impairment of plasminogen binding to fibrin at high fibrinogen concentration, was observed.

STUDY 8

Composition of HFLT Clots

The composition of fibrin clots formed with normal fibrinogen at various concentrations of fibrinogen (2–5 mg/ml) and thrombin (0.005–0.1 U/ml) were analyzed (Table 5). The content of fibrin I (DesAA-fibrinogen), fibrin II (desAABB-fibrinogen), and fibrinogen was determined from fibrinopeptide release data. As shown in Table 5, the clots contained mostly fibrin II at 0.1 U/ml thrombin, but at low thrombin concentrations (0.005 and 0.01 U/ml), more fibrin I and intact fibrinogen were observed in the clots with increasing fibrinogen. Fibrin clots made with 5 mg/ml fibrinogen and 0.005 U/ml thrombin contained 18% fibrin II, 45% fibrin I and 37% fibrinogen, even after overnight incubation at 37° C.

TABLE 5

Composition of Fibrin Clots With Low Concentration of Thrombin

| Thrombin (U/ml) | Fbg (mg/ml) | DesAABB Fbg | DesAA Fbg | Fbg |
|---|---|---|---|---|
| | | % | | |
| 0.1 | 1 | 100 | | |
| | 3 | 100 | | |
| | 5 | 100 | | |
| 0.01 | 1 | 84 | 16 | 0 |
| | 3 | 48 | 45 | 7 |
| | 5 | 27 | 59 | 14 |
| 0.005 | 1 | 49 | 51 | 0 |
| | 3 | 18 | 56 | 26 |
| | 5 | 10 | 52 | 38 |

STUDY 9

Fibrinolytic Properties of HFLT Fibrin Clots

Fibrin clots made with different concentrations of thrombin and normal fibrinogen, as described above, were analyzed for t-PA binding, plasminogen binding, and clot dissolution by plasmin. Direct binding studies showed that t-PA binding to the clots did not differ significantly with increasing fibrinogen and decreasing thrombin concentrations, while plasminogen binding decreased.

When fibrin monomers were repolymerized in the presence of increasing fibrinogen concentration, plasminogen binding to fibrin decreased (Table 6). A 16 mg/ml stock solution of soluble fibrin II monomers in 20 mM acetic acid was diluted with plasminogen 1 in Tris-Tween buffer to give final concentrations of 2 mg/ml fibrin and 0.1 mg/ml plasminogen 1. Various concentrations of fibrinogen were also present. The fibrin monomers spontaneously polymerized due to the neutral pH. The unbound fraction of plasminogen 1 was determined as described above.

TABLE 6

Inhibition of Plasminogen Binding To Fibrin By Normal Fibrinogen

| | Normal Fibrinogen Added (mg/ml) | | | | |
|---|---|---|---|---|---|
| | 0 | 1 | 2 | 3 | 4 |
| | % Bound | | | | |
| Plg 1 | 30 | 23 | 10 | 5 | 4 |

Plasmin degradation of fibrin clots with a high content of fibrinogen was also slower than that of clots containing mostly fibrin II. Thus, this study shows that fibrin clots made with high fibrinogen and low thrombin concentration have impaired plasminogen and plasmin interaction with fibrin.

Equivalents

Those skilled in the art will recognize, or be able to ascertain using no more than routine experimentation, many equivalents to the specific embodiments of the invention described herein. Such equivalents are intended to be encompassed by the claims.

We claim:

1. A method for thrombolytic therapy in a mammal comprising administering to the mammal a plasminogen activator and glu plasminogen 2.

2. The method of claim 1, wherein the mammal is a human.

3. The method of claim 1, wherein the glu plasminogen 2 is recombinant glu plasminogen 2.

4. The method of claim 1 wherein the plasminogen activator and glu plasminogen 2 are administered separately.

5. The method of claim 1 wherein the plasminogen activator and glu plasminogen 2 are administered as a pharmaceutical composition comprising plasminogen activator, and glu plasminogen 2.

6. The method of claim 1 wherein the plasminogen activator is tissue plasminogen activator.

7. A method for thrombolytic therapy in a human comprising administering to the human tissue plasminogen activator and glu plasminogen 2.

8. A pharmaceutical composition comprising a plasminogen activator and glu plasminogen 2.

9. The pharmaceutical composition of claim 8 wherein the plasminogen activator is tissue plasminogen activator.

10. A method for thrombolytic therapy in a mammal having a condition selected from the group consisting of:
    (a) abnormally high plasma levels of fibrinogen; and
    (b) mutant fibrinogen which is resistant to cleavage by thrombin;
comprising administering to the mammal a plasminogen activator and glu plasminogen 2.

11. The method of claim 10 wherein the mammal is a human.

12. The method of claim 10 wherein the glu plasminogen 2 is recombinant glu plasminogen 2.

13. The method of claim 10 wherein the glu plasminogen 2 and plasminogen activator are administered separately.

14. The method of claim 10 wherein the glu plasminogen 2 and plasminogen activator are administered as a pharmaceutical composition comprising glu plasminogen 2 and plasminogen activator.

15. The method of claim 10 wherein the plasminogen activator is tissue plasminogen activator.

16. A method for thrombolytic therapy in a human having a condition selected from the group consisting of:
    (a) abnormally high plasma levels of fibrinogen; and
    (b) mutant fibrinogen which is resistant to cleavage by thrombin;
comprising administering to the human tissue plasminogen activator and glu plasminogen 2.

* * * * *